United States Patent [19]

Meglasson

[11] Patent Number: 5,134,164

[45] Date of Patent: Jul. 28, 1992

[54] USE OF 3-GUANIDINOPROPIONIC ACID IN THE TREATMENT OF EXCESS ADIPOSITY

[75] Inventor: Martin D. Meglasson, Kalamazoo, Mich.

[73] Assignee: The Upjohn Company, Kalamazoo, Mich.

[21] Appl. No.: 780,432

[22] Filed: Aug. 14, 1991

Related U.S. Application Data

[63] Continuation of Ser. No. 486,615, Feb. 28, 1990, abandoned.

[51] Int. Cl.$^5$ .................. A61K 31/195; A61K 31/19; A61K 31/155
[52] U.S. Cl. .................................. 514/565; 514/557; 514/634
[58] Field of Search .................. 514/565, 557, 634

[56] References Cited

FOREIGN PATENT DOCUMENTS

| 891509 | 1/1972 | Canada ........................... 260/293.2 |
| 1153424 | 5/1969 | United Kingdom . |
| 1195199 | 6/1970 | United Kingdom . |
| 1195200 | 6/1970 | United Kingdom . |
| 1552179 | 9/1979 | United Kingdom . |

OTHER PUBLICATIONS

A. Aynsley-Green and K. G. M. M. Alberti, "In Vivo Stimulation of Insulin Secretion by Guanidine Derivatives in the Rat", Horm. Metab. Res. 6:115-120 (1974).
F. Blachier, et al., "Stimulus-Secretion Coupling of Arginine-Induced Insulin Release. Uptake of Metabolized and Nonmetabolized Cationic Amino Acids by Pancreatic Islets", Endocrinology 124:134-141 (1989).
J. J. Roberts and J. B. Walker, "Feeding a Creatine Analogue Delays ATP Depletion and Onset of Rigor in Ischemic Heart", Am. J. Physiol. 243:H911-H916 (1982).
T. S. Moerland, et al., "Administration of a Creatine Analogue Induces Isomyosin Transitions in Muscle", Am. J. Physiol. 257:C810-C816 (1989).
E. A. Shoubridge, et al., "Biochemical Adaptation in the Skeletal Muscle of Rats Depleted of Creatine with the Substrate Analogue $\beta$-Guanidinopropionic Acid", Biochem. J. 232:125-131 (1985).
D. A. Mahanna, et al., "Effects of $\beta$-Guanidinopropionic Acid on Murine Skeletal Muscle", Exper. Neurol. 68:114-121 (1980).
R. P. Shields, et al., "Skeletal Muscle Function and Structure after Depletion of Creatine", Lab. Invest. 33:151-158 (1975).

Primary Examiner—Frederick E. Waddell
Assistant Examiner—K. Weddington
Attorney, Agent, or Firm—Debbie K. Wright; Lawrence T. Welch

[57] ABSTRACT

The present invention provides a method for treating or preventing certain metabolic disorders comprising the systemic administration of 3-guanidinopropionic acid.

5 Claims, No Drawings

USE OF 3-GUANIDINOPROPIONIC ACID IN THE TREATMENT OF EXCESS ADIPOSITY

This is a continuation of Ser. No. 07/486,615, now abandoned.

FIELD OF INVENTION

The present invention provides a new use for a known compound. More particularly, the present invention provides a method of treating or preventing certain metabolic disorders of human and animal metabolism, e.g., hyperglycemia, impaired glucose tolerance, hyperinsulinemia, insulin insensitivity, hyperamylinemia, excess adiposity or hyperlipidemia by the administration of 3-guanidinopropionic acid (3-GPA).

BACKGROUND OF THE INVENTION

There are several metabolic disorders of human and animal metabolism, e.g., hyperglycemia, impaired glucose tolerance, hyperinsulinemia and insulin insensitivity, hyperamylinemia, excess adiposity, and hyperlipidemia. Some or all of the above disorders may occur in the following disease states: non-insulin dependent diabetes mellitus (NIDDM), obesity, hypertension and atherosclerosis.

Hyperglycemia is a condition where the blood glucose level is above the normal level in the fasting state, following ingestion of a meal, or during a provocative diagnostic procedure, e.g., a glucose tolerance test. It can occur in NIDDM as well as obesity. Hyperglycemia can occur without a diagnosis of NIDDM. This condition is called impaired glucose tolerance or pre-diabetes. Impaired glucose tolerance occurs when the rate of metabolic clearance of glucose from the blood is less than that commonly occurring in the general population after a standard dose of glucose has been orally or parenterally administered. It can occur in NIDDM as well as obesity, pre-diabetes and gestational diabetes.

Hyperinsulinemia is defined as having a blood insulin level that is above normal level in the fasting state, following ingestion of a meal or during a provocative diagnostic procedure. It can be seen in NIDDM or obesity and can be associated with or causal in hypertension or atherosclerosis. Hyperinsulinemia can occur without a diagnosis of diabetes. It may occur prior to the onset of NIDDM. Insulin insensitivity, also called insulin resistance, occurs when the insulin-dependent glucose clearance rate is less than that commonly occurring in the general population during diagnostic procedures such as a hyperinsulinemic clamp or a minimal model test. See, e.g., Bergman, R. N. et al., J. Clin. Invest. 68:1456–1467 (1981). Insulin insensitivity is considered also t occur when the blood glucose concentration is higher than that commonly occurring in the general population after intravenous administration of insulin (insulin tolerance test) or when the ratio of serum insulin-to-glucose concentration is higher than that commonly occurring in the general population after a 10–16 hour fast. Insulin insensitivity may be found in NIDDM or obesity and can also be associated with or causal to hypertension or atherosclerosis.

Hyperamylinemia is defined as having an abnormally high blood amylin level. Amylin is also known as diabetes associated peptide (DAP) and insulinoma associated polypeptide (IAP). Hyperamylinemia can be seen in NIDDM or obesity.

Excess adiposity can be seen in NIDDM associated with obesity and obesity without NIDDM. It is defined as a higher fat body mass-to-lean body mass ratio than that commonly occurring in the general population as measured by whole body specific gravity or other generally accepted means.

Hyperlipidemia is defined as having an abnormal level of lipids in the blood. Hyperlipidemia exists when the serum concentration of total cholesterol or total triglycerides or the serum concentration of LDL-cholesterol/HDL-cholesterol is higher than that commonly occurring in the general population. It can be seen in NIDDM or atherosclerosis.

The above disease states could be treated by either ameliorating or preventing the metabolic and biochemical disorders. In addition, humans and animals, which have not been diagnosed as having one of the above disease states but evidencing some or all of the disorders described above, could be benefited by preventing the development of a currently recognized disease state. Therefore, a compound that is useful in the treatment of hyperglycemia, impaired glucose tolerance, hyperinsulinemia, insulin insensitivity, hyperamylinemia, excess adiposity or hyperlipidemia could also be used to treat or prevent NIDDM, obesity, hypertension or atherosclerosis.

3-Guanidinopropionic acid (3-GPA) is an endogenous metabolite found in animals and humans, See, e.g., Hiraga, Y. et al., J. Chromatography 342:269–275 (1985) and Watanabe, Y. et al., Guanidines, edited by Mori et al., Plenum, New York, pp. 49–38 (1983). The compound, which is available from Sigma Chemical Co., has been used extensively in the study of creatine metabolism and gamma-aminobutyric acid receptor function. See, e.g., Bowery, R. et al., Br. J. Pharmacol. 50:205–218 (1974). Except as noted below, these studies do not relate to 3-GPA's utility in treating human or animal disease.

Guanidine, monoguanidine and diguanidine compounds have been shown to produce hypoglycemia. See, e.g., Watanabe, C., J. Biol. Chem. 33:253–265 (1918); Bischoff, F. et al., Guanidine structure and hypoglycemia 81:325–349 (1929). However, these compounds were observed to be toxic. In 1957, biguanide derivatives, e.g. phenformin and metformin, were used clinically as anti-diabetic agents. Some members of this class continue to be used today while others have been withdrawn from the market or banned in the United States and most Western countries. See, e.g., Schafer, G., Diabete Metabol. (Paris) 9:148–163 (1983).

Gamma-guandinobutyramide also known as Tyformin, and the HCl salt of Tyformin, known as Augmentin, were investigated as potential anti-diabetic agents from the mid-1960's until the mid-1970's. Thile Augmentin produced hypoglycemia, it was reported to produce hypertension in dogs and respiratory and circulatory collapse in rats and rabbits. See, e.g., Buckle, A. et al., Horm. Metab. Res. 3:76–81 (1971). The free acid of the amide was said to lack hypoglycemic activity.

British patent 1,153,424 discloses the use of certain esters and amides of guanidino-aliphatic acids in the treatment of diabetes mellitus where hyperuremia is present. The patent does not disclose that these compounds have an effect on hyperglycemia or any other symptom or pathological state related to diabetes. In a Canadian patent, 891509, the use of esters and amides of guanidinoalphatic acids were disclosed for treating hyperuremia and hyperglycemia in diabetes mellitus. As noted above, the biologic activity of a guanidino alkanoic acid was known to be different and less favorable so as to be ineffective compared to its amide for treating hyperglycemia.

British patent, 1,195,199 discloses the use of guanidino alkanoic acids or their amides or esters in an insulin-containing, parenterally-administered composition for the treatment of hyperglycemia occurring in diabetes. According to this patent, the combining of a guanidino alkanoic acid, amide or ester with insulin reduces the risk of hypoglycemia as compared to insulin alone. British patent 1,195,200 discloses the use of guanidino alkanoic acids in a composition containing a guanidino alkanoic acid amide or esters derivative for the treatment of hyperglycemia occurring in diabetes. In a subsequent British patent, 1,552,179, the use of guanidino alkanoic acids, their salts, amides or esters in combination with a gluconeogenesis inhibitor for treating hyperglycemic conditions was disclosed. Metformin was cited as an inhibitor of gluconeogenesis. Biological data indicated that HL 523, the preferred guanidino alkanoic acid derivative, was inactive as a single agent in six of seven experiments where blood glucose concentration was measured in alloxan diabetic mice and only weakly active in the seventh study. Most notably, British patents 1,195,199, 1,195,200 and 1,552,179 do not claim utility for guanidino alkanoic acids, as the sole active component, in compositions for treating hyperglycemic symptoms in diabetes. Among the guanidino alkanoic acids tested, several were inactive as a single agent. Thus, a variety of guanidino alkanoic acids lack significant anti-diabetic activity and combination of these compounds with an agent of known anti-diabetic activity, e.g., metformin, is necessary to show beneficial activity.

Aynsley-Green and Alberti injected rats intravenously with 3-GPA, arginine, guanidine, 4-guanidinobutyramide, and 4-guanidinobutyric acid. Arginine and 3-GPA stimulated insulin secretion transiently, but did not affect the blood glucose concentration while the other compounds stimulated insulin secretion but produced a rise in blood glucose concentration. See, e.g., Aynsley-Green, A. et al., Horm. Metab. Res. 6:115–120 (1974). Blachier, et al., observed that 10 mM 3-GPA stimulated insulin secretion by isolated rat islets in vitro. See, e.g., Blachier, F. et al., Endocrinology 124:134–141 (1989). The insulin response induced by 3-GPA was 55% of that occurring when arginine was tested at the same concentration. In rats fed a died supplemented with 10 mg/g 3-GPA for 30–60 days, the heart glycogen content was increased. See, e.g., Roberts, J. et al., Am. J. Physiol. 243:H911–H916 (1982). Similarly, skeletal muscle glycogen content was increased in rats fed chow supplemented with 10 mg/g of 3 -GPA for 6–10 weeks. Mice fed a diet supplemented with 3-GPA at 20 mg/g and supplied with drinking water containing 5 mg/ml 3-GA for 7–12 weeks had serum glucose concentrations that did not differ significantly from mice receiving unsupplemented chow and water. See, e.g., Moerland, T. et al., Am. J. Physiol. 257:C810–C816 (1989).

With respect to adiposity, it is known that in some, but not all cases, supplementation of the diet with 10–20 mg/g 3-GPA results in decreased body weight. See, e.g., Moerland, supra and Mahanna, D. et. al., Exper. Neurol. 68:114–121 (1980). This effect has been attributed to decreased skeletal muscle mass and has not been attributed to reduced adiposity or decreased lipid storage. See, e.g., Mahanna, supra and Shields, R. et al., Lab. Invest. 33:151–158 (1975).

What is needed in the art is a sole therapy to treat or prevent the underlying metabolic disorders in these conditions.

INFORMATION DISCLOSURE STATEMENT

The following patents disclosed the use of guanidino-aliphatic acids or their amides or esters for the treatment of diabetes: British patent 1,153,424; Canadian patent 891509; British patent 1,195,199; British patent 1,195,200; British patent 1,552,179. None of these patents disclosed the use of a 3-GPA as a sole therapy. 3-GPA has been shown to stimulate insulin secretion without lowering blood glucose, See, e.g., Ansley-Green, A. et al., Horm. Metab. Res. 6:115–120 (1974) and Blachier, F., Endocrinology 124:134–141 (1989); and to increase heart glycogen content. See, e.g., Roberts, J., Am. J. Physiol. 243:H911–H916 (1982) and Moerland, T., Am. J. Physiol. 257:C810–C816 (1989). It is also known that supplementation of the diet with 3-GPA results in decreased body weight. See Shoubridge, E. A. et al., Biochem. J. 232:125–131 (1985); Moerland, supra; Mahanna, D. A. et al., Exper. Neurol. 68:114–121 (1980); and Shields, R. P. et al., Lab. Invest. 33:151–158 (1975). All of the references cited in this section are discussed above.

SUMMARY OF THE INVENTION

The present invention provides a method of treating or preventing a metabolic disorder selected from the group consisting of hyperglycemia, impaired glucose tolerance, hyperinsulinemia, hyperamylinemia, excess adiposity and/or hyperlipidemia in a patient susceptible to or experiencing said disorder comprising the systemic administration of 3-guanidinopropionic acid or a pharmacologically acceptable salt thereof, as the sole pharmaceutical agent effective to treat or prevent said condition.

Despite extensive suggestions in the literature that it would be ineffective as a sole therapy, surprisingly and unexpectedly, it has been found that 3-GPA causes several biologic effects that are beneficial in the treatment of human disease. It improves plasma glucose level, insulin sensitivity, plasma amylin level, adiposity and plasma lipid level. All of these effects are beneficial in treating NIDDM. 3-GPA offers therapeutic advantage over metformin, a compound currently used to treat NIDDM. See, e.g., Vigneri, R. et al., Diabetes Care 10:118–122 (1987). When administered to KKA$^y$ (Upjohn) diabetic mice, 3-GPA is more potent and produces a greater decrease in plasma glucose concentration.

NIDDM is characterized by hyperglycemia in the fasting or post-prandial state and impaired glucose tolerance after oral or parenteral administration of a glucose solution. 3-GPA, that has been administered to KKA$^y$ mice, a rodent model of NIDDM, decreases the non-fasting plasma glucose concentration and improves glucose tolerance. The minimum effective dose in KKA$^y$ mice is 130 mg/kg/d when administered as an admixture in rodent chow. Higher doses produce a proportionately greater effect. Doses that are less than the minimum effective dose in KKA$^y$ mice may be effective at decreasing blood glucose levels in other species, e.g., human, since elimination is rapid in rodents and may occur more slowly in other species.

Impaired tissue insulin sensitivity and hyperinsulinemia occur in NIDDM, hypertension (See, e.g., Reaven, supra), obesity (See, e.g., Glass A., supra), and atherosclerosis and may be etiological factors in these diseases. 3-GPA ameliorates hyperinsulinemia in KKA$^y$ mice and decreases the plasma ratio of insulin-to-glucose concentration, indicating increased insulin sensitivity. Therefore, 3-GPA is useful in the treatment or in the prevention of NIDDM, hypertension, obesity, and atherosclerosis.

Hyperamylinemia may occur in NIDDM, decreasing tissue glucose metabolism and altering pancreatic hormone secretion. 3-GPA ameliorates hyperamylinemia and therefore is beneficial in treating disease states in which plasma amylin concentration is increased.

Excess adiposity is an etiological factor in NIDDM and when extreme, represents a disease state in itself. 3-GPA decreases adiposity by decreasing the level of lipids stored in fat and liver tissue. The compound is therefore beneficial in the treatment of obesity alone or in concert with NIDDM. The effect of 3-GPA is selective for lipid-rich tissues (e.g., epididymal fat and fatty liver of ob/ob mice) while muscle mass is unaffected or only minimally affected.

Increased serum low density lipoprotein (LDL) cholesterol concentration is an etiological factor in coronary artery disease. 3-GPA decreases LDL-cholesterol levels in spontaneously hyperlipidemic mice and therefore is useful in treating or preventing hyperlipoproteinemia, atherosclerosis and coronary artery disease.

By sole active pharmaceutical agent is meant that the 3-GPA compound or its salt, administered as claimed herein, is the only pharmaceutical agent administered to the patient which has an effect on the metabolic disorders described herein.

By patients susceptible to or experiencing a metabolic disorder, i.e., hyperglycemia, impaired glucose tolerance, hyperinsulinemia, insulin insensitivity, hyperamylinemia, excess adiposity and/or hyperlipidemia is means a patient who exhibits said metabolic disorder and is therefore likely to exhibit one of more of the disease states described above. Such patients are readily diagnosed by a physician of ordinary skill.

By treatment is meant the amelioration or total avoidance of the metabolic disorder as described herein. By prevention is meant the avoidance of a currently recognized disease state, as described herein, in a patient evidencing some or all of the metabolic disorders described above.

For all of these purposes, any convenient route of systemic administration is employed, e.g., orally, parenterally, intranasally or intrarectally. In general, the preferred form of administration is orally.

The above compositions may be administered in a sustained release formulation. By sustained release is meant a formulation in which the drug becomes biologically available to the patient at a measured rate over a prolonged period. Such compositions are well-known in the art.

The dosage regimen for 3-GPA in accord with this invention will depend on body weight. 3-GPA, in pharmaceutical dosage form, can range from 1–400 mg/kg/day. The preferred dose is 5–100 mg/kg/day. Any sustained released formulations can be made.

3-GPA is ineffective when administered to rodents in a state similar to insulin-dependent diabetes mellitus. 3-GPA did not alter the non-fasting plasma glucose level in lean, normoglycemic C57BL6Job/? mice (Jackson Laboratory) when administered as a 2mg/g admixture in chow for 13 days. At a higher level, 10 mg/g, 3-GPA did not affect plasma glucose concentration when administered to C57BL6Job/? mice for 4 days, but after administration for 13 days, plasma glucose concentration was decreased. The dose of 3-GPA that produced lower plasma glucose levels in C57BL6Job/? mice was >6 g/kg body weight/day. By contrast, a much lesser dose (130 mg/kg/d) produced an antihyperglycemic effect in diabetic KKA$^y$ mice. Since, 3-GPA decreases plasma glucose levels that are elevated, but has little effect at normal plasma glucose concentration, 3-GPA has a great therapeutic benefit in that it ameliorates hyperglycemia with little risk of hypoglycemic reactions in case of overdose.

DETAILED DESCRIPTION OF THE INVENTION

The present invention is seen more fully by the examples given below.

Example 1 Improvement of Plasma Glucose Level

To test the effect of 3-GPA on non-fasting plasma glucose concentration in KKA$^y$ mice, the mice are administered 3-GPA admixed in rodent chow for 4 days. Plasma is prepared from blood collected by puncturing the retro-orbital sinus of conscious mice that are in the ad libitum fed state. Blood samples are obtained on day 0 (prior to treatment) and on day 4 of treatment. Plasma is measured by an enzyme coupled assay using hexokinase and glucose-6-phosphate dehydrogenase. Data is shown as a means ±S.E.M. for 5 mice per group. Doses that produce a reduction in plasma glucose of 20% or greater are considered to have had a biologically meaningful effect. The percentage reduction in plasma glucose levels by 3-GPA is as follows: 0.8 mg/g, 20%; 1.5 mg/g, 48%; 2 mg/g, 52%; 10 mg/g, 77%. The results are summarized in Table I. 3-GPA also decreased the non-fasting plasma glucose level in obese, hyperglycemic C57BL6Job/ob mice which are considered to be a model of NIDDM.

To test the effect of 3-GPA on glucose tolerance in KKA$^y$ mice, the mice are administered 3-GPA admixed in rodent chow at 10 mg/g for 14 days or received unsupplemented chow. Blood samples are collected and plasma analyzed for glucose as described in legend to Table 1. Blood is collected at time 0 (prior to glucose administration) and at intervals after injection of 1.5 g/kg glucose intraperitoneally. Data, as seen in Table II, is shown as means ±S.E.M. for 5–6 mice per group.

Example 2 Improvement in Insulin Sensitivity

Data supporting the utility of 3-GPA in improving insulin sensitivity and ameliorating hyperinsulinemia is shown in Table III. KKA$^y$ mice are fed chow supplemented with 10 mg/g 3-GPA for 14 days or unsupplemented chow. Blood samples are obtained and analyzed for glucose as described in legend to Table I. Plasma insulin is determined using a single antibody radioimmunoassay technique. Data is shown as means ±S.E.M. for 5–6 mice/group.

Example 3 Improvement of Plasma Amylin Level

KKA$^y$ mice receive 3-GPA as a 2 mg/g admixture in chow or unsupplemented chow for 4 days. Ob/ob mice receive 3-GPA as a 2 or 10 mg/g admixture in chow or unsupplemented chow for 30 days. Blood samples are obtained as described in Table I. Amylin is measured in plasma using a double antibody radioimmunoassay. Results are shown in Table IV.

Example 4 Improvement in Adiposity

The effect of 3-GPA on body and organ weights is tested in ob/ob mice. The mice receive 3-GPA as a 2 mg/g or 10 mg/g admixture in chow or are fed unsupplemented chow. Data, which is seen in Table V, is shown as means ±S.E.M.

Example 5 Improvement in Plasma Lipid Level

Ob/ob mice receive 3-GPA as a 10 mg/g admixture in chow for 13 days or are fed unsupplemented chow. Plasma for lipoprotein analysis is obtained as described in Table I. Lipoprotein levels are determined with a Demand Autoanalyzer. Data, which is shown in Table VI, is seen as means ±S.E.M. for 5 mice per group. For comparison, the plasma lipoprotein profile is shown for 4 lean, non-diabetic C57BL6Job/? mice that are untreated.

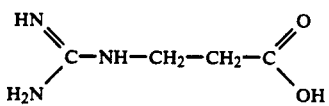

FORMULA

TABLE 1

| 3-GPA Admixture in Chow (mg/g) | Average dose (g/kg/d) | Non-Fasting Plasma Glucose (mg/dl) Days of Treatment | |
|---|---|---|---|
| | | 0 | 4 |
| Experiment 1 | | | |
| Nil | 0 | 481 + 59 | 651 + 52 |
| 2 | 0.32 | 441 + 68 | 313 + 75* |
| 10 | 1.74 | 464 + 67 | 148 + 5** |
| *P = 0.006. **P = 0.000. | | | |
| Experiment 2 | | | |
| Nil | 0 | 628 + 77 | 536 + 49 |
| 0.8 | 0.13 | 617 + 58 | 429 + 52* |
| 1.5 | 0.21 | 624 + 64 | 279 + 49** |

*P = 0.17. **P = 0.006

TABLE 2

| Time (min) | Plasma Glucose (mg/dl) | | P-value |
|---|---|---|---|
| | Control | 3-GPA | |
| 0 | 484 + 101 | 171 + 21 | 0.014 |
| 15 | 842 + 83 | 230 + 40 | 0.000 |
| 30 | 527 + 81 | 270 + 31 | 0.014 |
| 60 | 430 + 51 | 190 + 19 | 0.002 |
| 120 | 327 + 54 | 153 + 18 | 0.013 |

TABLE 3

| | Plasma Insulin (microunits/ml) | Plasma Insulin/Glucose (microunits/mg) |
|---|---|---|
| Control | 3,009 + 419 | 7.30 + 1.57 |
| 3-GPA | 299 + 117* | 2.04 + 0.83** |

*P = 0.000; **P = 0.016

TABLE 4

| Strain | Treatment | Plasma Amylin (ng/ml) |
|---|---|---|
| KKAy | control | 15.0 + 4.1 (n = 5) |
| | 3-GPA | 4.3 + 0.6 (n = 3) |
| ob/ob | control | 1.3 + 0.2 (n = 6) |
| | 3-GPA (2 mg/g) | 1.8 + 0.2 (n = 3) |
| | 3-GPA (10 mg/g) | 0.46 + 0.05 (n = 5) |

TABLE 5

| Experiment 1. 31 days treatment. 4–6 mice/group | | | |
|---|---|---|---|
| Concentration in Chow: | 0 | 2 mg/g | 10 mg/g |
| Body Weight (g) | 52.3 + 0.7 | 49.4 + 1.1 | 36.1 + 1.5 |
| Liver (g) | 4.3 + 0.2 | 3.6 + 0.1 | 1.6 + 0.2 |
| Epididymal Fat (g) | 3.7 + 0.1 | 3.8 + 0.3 | 2.5 + 0.2 |
| Experiment 2. 13 days treatment. 5 mice/group | | | |
| Concentration in Chow: | 0 | | 10 mg/g |
| Body Weight (g) | 43.4 + 1.3 | | 36.8 + 1.3 |
| Liver (g) | 2.4 + 0.2 | | 1.3 + 0.1 |
| Heart (g) | 0.11 + 0.01* | | 0.10 + 0.004 |
| Diaphragm (g) | 0.065 + 0.004 | | 0.061 + 0.004 |
| Calf muscle (g) | 0.050 + 0.001 | | 0.047 + 0.003 |

TABLE 6

| Phenotype: 3-GPA | ob/? (−) | ob/ob (−) | ob/ob (+) | P-value ob/ob (−) vs (+) |
|---|---|---|---|---|
| Cholesterol: | | | | |
| Total | 114 + 4 | 213 + 12 | 214 + 7 | 0.932 |
| Alpha | 96 + 3 | 194 + 15 | 204 + 9 | 0.660 |
| Beta | 18 + 1 | 19 + 4 | 10 + 3 | 0.044 |
| Triglyceride | | | | |
| Total | 112 + 10 | 170 + 41 | 149 + 25 | 0.656 |
| Alpha | 70 + 3 | 87 + 4 | 99 + 9 | 0.078 |
| Beta | 42 + 7 | 83 + 38 | 51 + 24 | 0.464 |

I claim:

1. A method of treating excess adiposity in a patient experiencing excess adiposity comprising the systemic administration to said patient of an amount effective to treat excess adiposity of 3-guanidinopropionic acid or a pharmaceutically acceptable salt thereof.

2. A method according to claim 1 wherein the mode of administration is oral.

3. A method according to claim 1 wherein said effective amount of 3-GPA ranges from 1–500 mg/kg/day.

4. A method according to claim 3 wherein said effective amount of 3-GPA ranges from 5–100 mg/kg/day.

5. A method of claim 1, wherein the 3-guanidinopropionic acid is administered to treat excess adiposity.

* * * * *